(12) United States Patent
Wacker et al.

(10) Patent No.: US 10,953,103 B2
(45) Date of Patent: Mar. 23, 2021

(54) COMPOSITION COMPRISING A BIOCOMPATIBLE AND BIODEGRADABLE POLYMER, NANOCARRIERS AND A DRUG AND METHODS OF MAKING AND USING THE SAME

(71) Applicant: Fraunhofer-Gesellschaft zur Förderung der angewandten Forschung e.V., Munich (DE)

(72) Inventors: Matthias Wacker, Frankfurt (DE); Susanne Beyer, Frankfurt (DE); Michael Parnham, Bad Soden/Ts. (DE); Werner Mäntele, Kiefersfelden (DE); Li Xie, Frankfurt am Main (DE); Vitali Vogel, Frankfurt am Main (DE)

(73) Assignee: Fraunhofer-Gesellschaft zur Förderung der angewandten Forschung e.V, Munich (DE)

( * ) Notice: Subject to any disclaimer, the term of this patent is extended or adjusted under 35 U.S.C. 154(b) by 0 days.

(21) Appl. No.: 15/773,696

(22) PCT Filed: Nov. 4, 2016

(86) PCT No.: PCT/EP2016/076715
§ 371 (c)(1),
(2) Date: May 4, 2018

(87) PCT Pub. No.: WO2017/077066
PCT Pub. Date: May 11, 2017

(65) Prior Publication Data
US 2018/0318433 A1 Nov. 8, 2018

(30) Foreign Application Priority Data
Nov. 6, 2015 (EP) .................................. 15193382

(51) Int. Cl.
*A61K 47/64* (2017.01)
*A61K 47/36* (2006.01)
(Continued)

(52) U.S. Cl.
CPC ............ *A61K 47/64* (2017.08); *A61K 9/0024* (2013.01); *A61K 38/215* (2013.01); *A61K 47/36* (2013.01);
(Continued)

(58) Field of Classification Search
None
See application file for complete search history.

(56) References Cited

U.S. PATENT DOCUMENTS

| 4,526,938 A | 7/1985 | Churchill |
| 4,774,091 A | 9/1988 | Yamahira |

(Continued)

FOREIGN PATENT DOCUMENTS

| KR | 20080024594 A | 3/2008 |
| WO | 9742940 | 11/1997 |

(Continued)

OTHER PUBLICATIONS

Doane et al., "Nanoparticle mediated non-covalent drug delivery", ADv Drug Deliv Rev. May 2013: 65(5): 607-621. (Year: 2013).*
(Continued)

*Primary Examiner* — Kyung S Chang
(74) *Attorney, Agent, or Firm* — Saffire IP; Daren P. Nicholson

(57) ABSTRACT

The present invention pertains to a composition comprising at least one biocompatible and biodegradable polymer, the polymer further comprising nanocarriers wherein the nanocarriers comprise a drug. Moreover, also encompassed by
(Continued)

Figure 1:
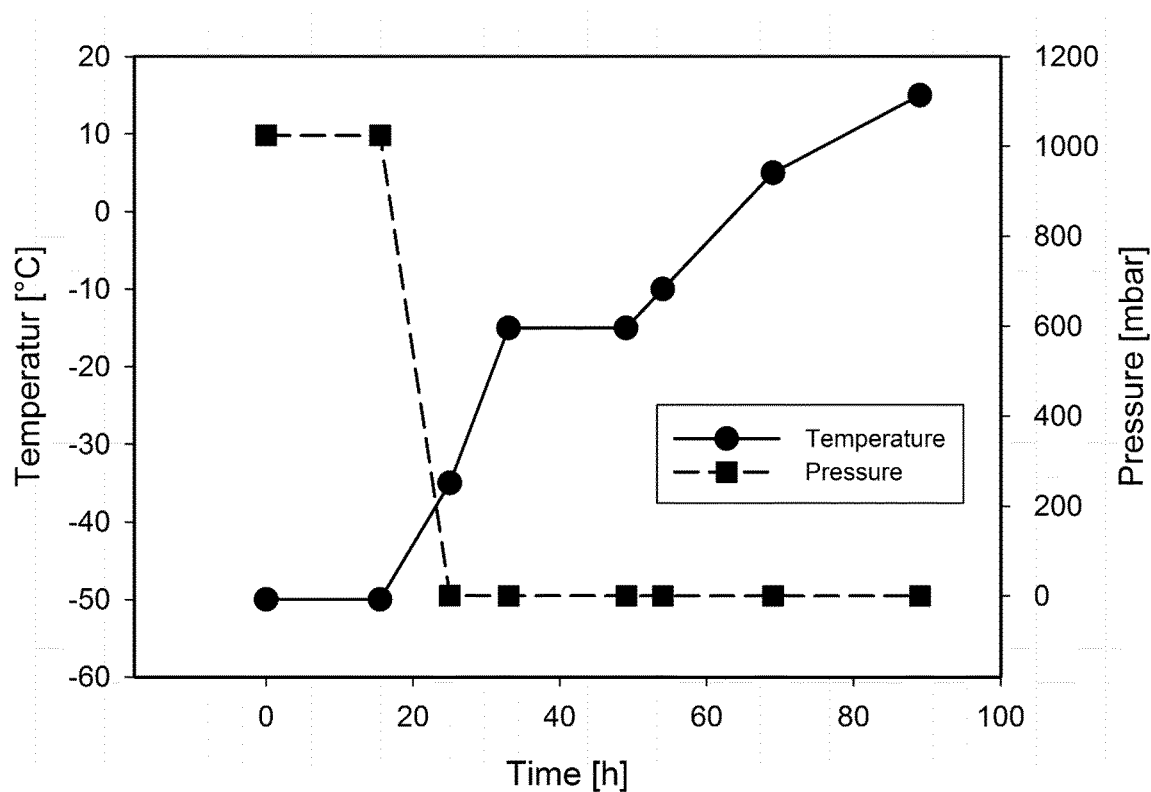

the invention is the use of the composition in the treatment of a disease and a method for manufacturing the composition.

11 Claims, 11 Drawing Sheets

(51) Int. Cl.

| | |
|---|---|
| *A61K 47/61* | (2017.01) |
| *A61K 47/69* | (2017.01) |
| *A61K 9/00* | (2006.01) |
| *A61K 38/21* | (2006.01) |
| *A61P 37/00* | (2006.01) |
| *A61P 25/00* | (2006.01) |
| *A61K 47/38* | (2006.01) |
| *A61K 47/50* | (2017.01) |

(52) U.S. Cl.
CPC .............. *A61K 47/38* (2013.01); *A61K 47/50* (2017.08); *A61K 47/61* (2017.08)

(56) References Cited

U.S. PATENT DOCUMENTS

| | | | | |
|---|---|---|---|---|
| 5,869,103 | A | 2/1999 | Yeh | |
| 6,020,004 | A | 2/2000 | Shah | |
| 6,555,156 | B1 | 4/2003 | Loughman | |
| 2002/0019336 | A1 | 2/2002 | Kitagawa | |
| 2003/0031701 | A1 | 2/2003 | Burke | |
| 2003/0041602 | A1 | 3/2003 | Williams | |
| 2004/0197413 | A1 | 10/2004 | Sheu | |
| 2004/0247683 | A1 | 12/2004 | Popescu | |
| 2005/0152980 | A1 | 7/2005 | Ausborn | |
| 2006/0141041 | A1 | 6/2006 | Tracy | |
| 2006/0210641 | A1 | 9/2006 | Shalaby | |
| 2008/0299177 | A1* | 12/2008 | Hardy ................ | A61K 9/0009 424/427 |
| 2009/0004118 | A1* | 1/2009 | Nie .................... | A61K 49/0002 424/9.35 |
| 2012/0213812 | A1* | 8/2012 | Lipford ............... | A61P 31/00 424/193.1 |
| 2014/0127301 | A1* | 5/2014 | Alexis .................. | A61K 39/00 424/489 |

FOREIGN PATENT DOCUMENTS

| | | |
|---|---|---|
| WO | 9902135 | 1/1999 |
| WO | 2001058474 | 8/2001 |
| WO | 2011072399 | 6/2011 |
| WO | 2012162555 | 11/2012 |

OTHER PUBLICATIONS

Ding et al., "Noncovalent interaction-assisted polymeric micelles for controlled drug delivery", Chem. Commun., 2014, 50, 11274. (Year: 2014).*

NIH Public Access—"Nanoparticle mediated non-covalent drug delivery", 2013, 65(5): 607-621 (Year: 2013).*

Ding et al. "Noncovalent interaction-assited polymeric micelles for controlled drug delivery", ChemComm, 2014, 50, pp. 11274-11290 (Year: 2014).*

Stanwick, Jason C., "Enhanced neurotrophin-3 bioactivity and release from a nanoparticle-loaded composite hydrogel," Journal of Controlled Release, vol. 160, No. 3, Jun. 2012, pp. 666-675.

PCT International Search Report PCT/US2016/076715, dated Dec. 23, 2016, EPO, Rijswijk, NL.

PCT Written Opinion of the ISA PCT/US2016/076715, dated Dec. 23, 2016, EPO, München, DE.

Portaccio et al. (2009), Improving compliance with interferon-β therapy in patients with multiple sclerosis. CNS drugs 23(6), 453-462.

Kempe et al. (2012), In situ forming implants—an attractive formulation principle for parenteral depot formulations. J Control Release 161(2), 668-679.

Boddohi S et al. (2009), Polysaccharide-based polyelectrolyte complex nanoparticles from chitosan, heparin, and hyaluronan. Biomacromolecules 10(6), 1402-1409.

Sax et al. (2012), Release pathways of interferon alpha2a molecules from lipid twin screw extrudates revealed by single molecule fluorescence microscopy. J Control Release 162(2), 295-302.

Sinha et al. (2003), Biodegradable microspheres for protein delivery. J Control Release 90(2003), 261-280.

Schliecker et al. (2003), In vitro and in vivo correlation of buserelin release from biodegradable implants using statistical moment analysis. J Control Release 94 (2004) 25-37; doi: 10. 1016/j.jconrel.2003.09.003.

* cited by examiner

A.

B.

C.

COMPOSITION COMPRISING A BIOCOMPATIBLE AND BIODEGRADABLE POLYMER, NANOCARRIERS AND A DRUG AND METHODS OF MAKING AND USING THE SAME

The present invention pertains to a composition comprising at least one biocompatible and biodegradable polymer, said polymer further comprising nanocarriers wherein said nanocarriers comprise a drug. Moreover, also encompassed by the invention is the use of said composition in the treatment of a disease and a method for manufacturing said composition.

For the treatment of a variety of diseases, low drug dosing frequencies as well as a controlled and prolonged release of a drug over time are desired. Continuous release formulations based on biocompatible substances are well known in the art. These formulations often contain solid microparticles or nanoparticles formed of the combination of biodegradable, synthetic polymers such as poly(lactic acid) (PLA), poly(glycolic acid) (PGA), and copolymers thereof encapsulating an active ingredient. While the polymers undergo hydrolysis in vivo, the entrapped drug is slowly released and the remaining polymer degradation products are fully absorbed by the body.

Next to polymer-based microparticles, formulations containing lipid-based microparticles (liposomes) are also frequently used. Liposomes usually consist of middle sized, compact phospholipid vesicles with one or up to few lipid bilayers which are sterically stabilized with a small amount of large-head phospholipids. For drug delivery, liposomes are often constructed with an additional layer of polyethylene glycol (PEG) at the outside which allows for longer circulatory life in the body (Blume et al., 1990).

Methods for producing polymeric or lipid-based microparticles as well as pharmaceutical compositions comprising such microparticles are extensively described in the prior art. Exemplary, the following documents are mentioned herein:

U.S. Pat. No. 6,020,004A reveals methods of making polymeric microparticles containing a drug wherein a mixture of the active ingredient and the polymer are dispersed within a continuous phase, the resulting dispersion is frozen, and the water and organic solvents are removed from the dispersion by lyophilization.

Another method for forming injectable microparticles comprising poly(lactic acid-co-glycolic acid) and the narcotic antagonist naltrexone was disclosed by Wise (Wise, 1984).

US2003031701A describes a method for producing an implantable polymer/drug matrix mass, comprising the steps of (1) forming a polymer solution/drug mixture comprising a polymer dissolved in an organic solvent and a suspended labile drug; (2) removing the solvent from the polymer solution/drug mixture, thereby forming a solid polymer/drug matrix; and (3) mechanically compressing the polymer/drug matrix, thereby forming an implantable polymer/drug matrix mass.

WO9742940 is concerned with a method for fabricating polymer-based controlled release devices comprising a solid polymer/drug matrix.

U.S. Pat. No. 6,555,156B describes a process for making for making encased bound microparticles by nebulizing a dispersion of the bound microparticles into a solution of an encasing polymer and into a liquid, non-solvent of said encasing polymer.

US2003041602A and US2004197413A reveal methods of forming micro- and nanoparticles by spray freezing into liquid and spray dry coacervation systems, respectively.

US2005152980A describes pharmaceutical microparticles consisting of a matrix with a mixture of at least one hydrophobic, biologically degradable polymer and optionally at least one water-soluble polymer, a pharmaceutical active ingredient distributed in the matrix, and in addition at least one water-insoluble, surface-active substance from the group of lecithins and phospholipids, distributed in the matrix, and a three-phase emulsion process for their preparation.

Microparticles comprising a mixture of a biodegradable polymer, a water soluble polymer, and an active agent are disclosed in U.S. Pat. No. 5,869,103A and US2006141041A.

U.S. Pat. No. 4,526,938A reveals a pharmaceutical compositions comprising a pharmacologically active polypeptide and a pharmacologically or veterinarily acceptable amphipathic, non-cross-linked linear, branched or graft block copolymer.

US2002019336A relates to a composition for sustained drug release including a mucopolysaccharide, a carrier protein, and a drug.

US2006210641A pertains to a sustained release complex of one or more peptides, one or more proteins or a combination thereof immobilized on an absorbable polymer microparticle optionally having an absorbable polymer coating.

WO9902135A1 describes microparticles being made up of a core comprising a component which is essentially of proteic nature and a natural, synthetic or semisynthetic polymer, and of an outside layer consisting of natural, synthetic or semisynthetic molecules that can be recognized by receptors or components of cell surface of living beings, or that can recognize natural, synthetic or semisynthetic molecular structures.

U.S. Pat. No. 4,774,091A describes a solid sustained-release preparation in the form of a needle-like or bar-like shape, which consists essentially of an active ingredient and a pharmaceutically acceptable biodegradable carrier that can be administered by injection or or implanted into the body.

US2004247683A relates to nanoparticles of a biodegradable polymer containing a hydrophilic, cationic drug, like streptomycin and pharmaceutical preparations containing the nanoparticles which are preferably administered orally.

All of the current formulations have certain limitations or drawbacks, especially regarding the stability of peptide- or protein-based drugs and thus a prolonged release. Peptide or protein-based drugs cannot be administered orally in an unprotected state due to the rapid degradation that occurs in the digestive tract. In addition, peptides or proteins usually have short half-lives in vivo, so that multiple injections of the drug or implants are necessary.

Concerning the protein-based drug interferon beta (IFN-β), there is still no formulation on the market that assures a prolonged release of IFN-β and therefore overcomes the obstacles that occur in the treatment with the currently approved products.

IFN-β has been approved for the treatment of relapsing remitting multiple sclerosis (RRMS) and secondary progressive MS (SPMS) (I.M.S.S. Group, 1993; Li et al., 2001b). The mode of action of this cytokine is complex but part of it can be explained by its anti-inflammatory and anti-proliferative activity that is correlated to a pleiotropic effect on the immune system and the blood-brain-barrier (Hohlfeld et al., 1997). IFN-β binds to the Interferon-α/β receptor and activates JAK1 and TYK2. The induced tyrosyl phosphorylation of transcription factor STAT1 and STAT2 results in an activation or repression of approximately 1,000 genes by interaction with the DNA (Reder et al, 2014; Sadzak et al., 2008).

RRMS is characterized by exacerbations or relapses over periods of at least 24 hours that are followed by periods of remission where symptoms improve or even disappear (Goldenberg, 2012). In SPMS, primary progressive MS with gradual aggravation of symptoms is diagnosed in the first place but over time patients experience relapses typical for RRMS (Goldenberg, 2012).

Currently, IFN-β is administered parenterally either by intramuscular (i.m.) or subcutaneous (s.c.) injection. Avonex® containing IFN-β-1a is injected intramuscularly and requires a dose of 30 µg once per week for adults (EMA, 2011). Rebif® also contains IFN-β-1a, but for this product the suggested dosing regimen is 44 µg three times a week administered by s.c. injection (EMA, 2014). However, parenteral application is known to be problematic since the pain caused by the injection is often associated with fear and discomfort for the patient. Hence, compliance might be harmed which can limit the beneficial effects of the prescribed medication. Still s.c. injection is most often easier to perform for a patient without assistance. However, referring to the commercially available products, the compromise is to perform the injection in a higher frequency than for the i.m. administered product. Moreover, the frequency of injection site reactions and other side effects of IFN-β-1a (leucopenia and liver function abnormalities) are higher after s.c. injection. On the other hand, flu-like syndrome which is the side effect with the highest prevalence in the treatment with IFN-β appears more often after i.m. injection (Langer-Gould et al., 2004; Portaccio et al., 2009). The most common signs are a mild fever reaction after the administration. Due to the dosing regimen that requires injection at least once a week, the discomfort of frequent injections might harm compliance of this very effective drug.

Implants appear to be a suitable technological approach towards a parenteral formulation with a rarer dosing frequency. Controlling the release of an API with a short half-life with the help of a polymer matrix can help to overcome fluctuations in the drug blood level that is often a drawback of immediate release formulations (Mank et al., 1991). Therefore, side effects can be minimized (Kempe et al., 2012).

However, implants suffer from other drawbacks like possible histological changes at the site of administration that can even develop into a fibrosis. Low molecular weight heparin has been demonstrated to prevent peritoneal, hepatic, and kidney fibrosis (Abe et al., 2007; Li et al., 2015; Pecly et al., 2006). Chemically, heparin is a glycosaminoglycan carrying negative charge. Disaccharide units of alternating glucosamine and glucuronic residues that are modified by carboxyl and sulfate groups are repeated 20 to 200-times by α-1, 4-linkage in the structure. Due to its negative charge, heparin is able to form nanocomplexes with positively charges molecules by electrostatic interactions. This method has been established for the preparation of protamine-heparin and chitosan-heparin nanocomplexes (Alam et al., 2015; Boddohi et al., 2009); Liang et al., 2000; Liu et al, 2007).

A multitude of biodegradable materials have been employed for the constitution of preformed implants including the polymers ethylene vinyl acetate, poly(lactic-co-glycolic acid), or triglycerides (Funk et al., 2005; Sax et al, 2012; Zhou et al., 1998). Methyl cellulose (MC) is known for its highly biocompatible and non-cell adhesive properties (Tate et al., 2001). MC exhibits inverse thermal gelling characteristics. An increased temperature results in a more viscous structure due to the diminished ability to form hydrogen bonds with the surrounding solvent (Li et al., 2001a; Sarkar et al., 1979). Moreover, salt concentration impacts the gelation behavior of MC. An elevated amount of electrolytes reduces the solubility of MC in water and therefore decreases the gelation temperature (Gupta et al., 2006). Gupta et al. established an in situ-forming implant by blending MC with hyaluronan (HA) for the intrathecal delivery of methylprednisolone and demonstrated that HA also lowers the gelation temperature of MC by acting as an anionic salt (Gupta et al., 2006). Moreover, HA has a pronounced hydrophobicity that can decrease water penetration into the drug delivery system (Spagnoli et al., 2005) and has beneficial effects on wound healing and scar formation due to its anti-inflammatory properties (Balazs et al., 1989; Sudha et al., 2014).

Although a multitude of biodegradable materials and methods for making preformed implants for controlled release of protein-based drugs are known, there is a strong need for improved formulations that overcome the obstacles that occur in the treatment with the currently approved products.

The technical problem underlying the present invention can be seen as the provision of means and methods for complying with the aforementioned needs. The technical problem is solved by the embodiments characterized in the claims and herein below.

The present invention pertains to a composition comprising at least one biocompatible and biodegradable polymer, said polymer further comprising nanocarriers wherein said nanocarriers comprise a drug.

The term "biocompatible" relates to a polymeric substance that may be inserted or injected into a living subject without causing an adverse response, for example an inflammatory response or acute rejection by the immune system. It is clear to the person skilled in the art that some degree of immune response is to be expected for substances that are highly compatible with living tissues. However, said immune responses shall be, preferably, insignificant. Methods of assessing the biocompatibility of materials are well known to the person skilled in the art and include LD50 testing and/or biochemical methods of toxicity assessment i.e. DNA synthesis, protein synthesis, and ATP activity as well as cell culture toxicity assays i.e. measurement of cell death after exposure to a substance.

The term "biodegradable" relates to a polymeric substance is susceptible to degradation by biological activity by lowering of the molar masses of macromolecules that form the substances. In vivo, the polymeric substance is hydrolyzed and the polymer degradation products are fully absorbed by the body over time. Degradation of a polymer may occur at varying rates, with a half-life in the order of days, weeks, months, or years, depending on several factors including polymer molecular weight and stereoregularity of the monomer subunits. Preferably, the half-life of a biodegradable polymer in accordance with the present invention is at about 1, at about 2, at about 3, at about 4, at about 5, at about 6 or at about 8 weeks. More preferably, the half-life is at about 2 weeks.

About as referred to herein refers to any specific value referred to in this specification, e.g., the indicated half-life times, including any variation which is within the range of +/−20%, +/−10%, +/−5%, +/−4%, +/−3%, +/−2% or +/−1%.

The term "polymer" as used herein refers to macromolecules composed of repeated subunits, the so-called monomers. Polymers may be typical synthetic plastics, e.g., polystyrene, but also include natural biopolymers, such as DNA and proteins. Natural occurring and synthetic polymers are generated via polymerization of monomers. The chemical reaction underlying the polymerization process depends on the nature of the monomers and the bonds formed between the monomers in the polymeric structure. Suitable chemical reactions that will give raise to polymeric structures are well known to those skilled in the art. Due to the large molecular mass, polymers have usually special and unique physical properties, including toughness, viscoelasticity, and tendencies to form glasses and semicrystalline structures rather than crystals. Preferably, the polymer according to the present invention comprises about 50 to 100,000 monomer subunits, about 100 to 50,000 monomer subunits, about 500 to 25,000 monomer subunits or about 1,000 to about 10,000 monomer subunits. The polymer according to the present invention is, preferably, slowly swelling under physiological conditions. "Slowly swelling under physiological conditions" as meant herein implicates that the biocompatible and biodegradable polymer undergo slow hydrolysis in vivo, thereby slowly releasing the nanocarriers comprising the drug. Polymer hydrolysis involves the scission of susceptible molecular groups by reaction with water. Polymer hydrolysis may be acid, base or enzyme catalyzed. The hydrolysis and degradation of a polymer may occur at varying rates, with a half-life in the order of days, weeks, months, or years, depending on several factors including polymer molecular weight and stereoregularity of the monomer subunits.

Biocompatible and biodegradable polymers are preferably selected from the group consisting of: polylactide (PLA), polyglycolide (PGA), polycaprolactone (PCL), polyhydroxyalkanoate (PHA), poly(ethylene-vinyl acetate) (PEVA), triglycerides, polysaccharides such as hyaluronic acid, cellulose esters and starch, proteins such as gelatin, and human or bovine serum albumin (HAS or BSA), and copolymers thereof. More preferably, the biocompatible and biodegradable polymer comprises a polysaccharide. Most preferably, the biocompatible and biodegradable polymer comprises methyl cellulose and/or hyaluronan.

Preferably, the polymer to be used in accordance with the present invention shall have a glass-transition temperature (i.e. the temperature at which the polymer has a tendency to form glass) less than 65° C. and, preferably, at about 40° C. to 60° C., preferably, about 45° C. to 55° C., and preferably about 50° C. In the case of proteins as biocompatible and biodegradable polymers according to the present invention, the polymers shall have, preferably, a glass-transition temperature at about 25° C. to 100° C., preferably at about 25° C. to 80° C., preferably at about 25° C. to 60° C., preferably at about 40° C. to 80° C., more preferably at about 40 to 60° C. Further details, in particular for BSA, may be found in Brownsey et al., 2003.

The composition of the present invention can be administered to a living organism by several administration routes known in the art. For example, the composition may be administered by intramuscular (i.m.) or subcutaneous (s.c.) injection or implanted into a living organism at a variety of sites within the body. Preferably, the composition of the present invention is processed into preformed implants and administered subcutaneously (s.c.) to a living organism. Preferably, said living organism is an animal, and more preferably, a mammal such as a human, primate, horse, sheep, goat, cow, dog, cat or rodent. Most preferably, the living organism is a human.

The term "nanocarrier" refers to a structural arrangement of a polymer, protein and/or lipid. Preferably, such a nanocarrier is a particle, preferably, a gel-like, liposome-like, micelle-like or solid particle. It will be understood by those skilled in the art, dependent on the nature of the compound or compounds and the methods used to form the nanocarrier, it will be determined whether the nanocarrier will form a gel-like, liposome-like, micelle-like or solid particle. Suitable methods and suitable compounds are well known to the skilled person.

Polymer-based nanocarriers of the present invention may be produced by methods known in the art are preferably selected from the group consisting of: precipitation, emulsion polymerization, interfacial condensation, freeze drying, supercritical fluid processing techniques, and coacervation. Solidification of the nanocarriers is preferably done by freezing, drying or freeze-drying. Commonly used polymers include polylactide (PLA), polyglycolide (PGA), polycaprolactone (PCL), polyhydroxyalkanoate (PHA), poly(ethylene-vinyl acetate) (PEVA), triglycerides, polysaccharides and proteins. Preferably, the polymer-based nanocarrier comprises heparin.

Lipid-based nanocarriers of the present invention preferably consist essentially of phospholipids. Encapsulation of drug solutions into lipid-based particles can be performed by methods known in the art, including high-pressure homogenization, microemulsion formation, emulsification-solvent evaporation (precipitation), solvent injection (or solvent displacement), phase inversion, and ultrasonication. Commonly used phospholipids to prepare liposomes include matrix lipids such as DPPC or DSPC, PEGylated lipids such as DSPE-PEG2000 for longer circulation in vivo, lipid bilayer destabilizing lipids, such as lyso-lecithin or pore forming photoactivable lipids and functionalized lipids such as maleimide-DSPE-PEG2000 for conjugating ligands such as antibodies and/or peptides for site-specific targeting.

The size of the nanocarrier ranges, typically, from about 5 to about 2,000 nm, preferably, 10 to about 1,000 nm, preferably, from about 50 to about 500 nm. The particle size and/or shape of the nanocarriers of the present invention may be determined by methods known in the art, for example dynamic light scattering and electron microscopy.

Preferably, the nanocarrier of the present invention is incorporated into the biocompatible and biodegradable polymeric matrix formed by the biocompatible and biodegradable polymer according to the invention. The nanocarriers are, preferably, covalently or non-covalently bound to the at least one biocompatible and biodegradable polymer. Non-covalent and covalent bonds are known in the art. Examples of non-covalent bonds include electrostatic interaction, van der Waals forces, hydrophobic effects, streptavidin-biotin interaction and antibody-antigen interaction. Covalent bonds are chemical bonds. The binding of the nanocarriers may, thus, be reversibly or non-reversibly. Reversibly bound nanocarriers are, e.g., released from the polymer by changes in the physiological surroundings, e.g., by an alteration in PH, ionic strength and the like. Non-reversibly bound nanocarriers will stick to the polymer and will become released from the polymeric matrix once the polymer becomes degraded. Alternatively, non-reversibly bound nanocarriers may be released by enzymatic cleavage of, e.g., a covalent bond between the nanocarrier and the polymer.

Typically, the nanocarriers may constitute from about 1% to 90%, more preferably, about 10% to 80%, about 20% to 70%, about 30% to 60% or from about 40% to 50% (weight/weight) of the entire composition.

The term "drug" in accordance with the present invention refers to an agent, or its pharmaceutically acceptable salt, which possesses therapeutic, prophylactic or diagnostic properties in vivo. The term drug as used herein can include any type of drug including, but not limited to, immunoglobulin-like proteins, antibodies, cytokines, interleukins, interferons, erythropoietin, nucleases, tumor necrosis factor, colony stimulating factors, insulin, enzymes, tumor suppressors, hormones, antigens growth factors, peptides, polypeptides and polynucleotides, such as antisense molecules. Furthermore, drugs may exhibit any type of activity including, but not limited to, modulation of the immune system, anti-cancer activity, anti-bacterial, anti-viral and anti-fungal activity. Preferably, the drug is a peptide- or protein-based drug that preferably functions as an immunomodulatory agent.

More preferably, the drug to be used in accordance with the present invention is interferon beta (IFN beta). IFN beta (IFN-β) belongs to the group of interferons. Interferons (IFNs) are signaling proteins that are made and released by host cells in response to the presence of several pathogens, such as viruses, bacteria, parasites, and also tumor cells. IFNs belong to the large class of proteins known as cytokines. Cytokines are important communication molecules used between cells to trigger the immune system to eradicate pathogens. More than twenty distinct IFN genes and proteins have been identified in animals, including humans. IFNs can be classified in three categories, type I, type II and type III, depending on the type of receptor through which they signal.

Type I interferons bind to a specific cell surface receptor complex known as the IFN-α/β receptor (IFNAR) that consists of IFNAR1 and IFNAR2 chains (De Weerd et al., 2007). IFN-α, IFN-β, IFN-ε, IFN-κ and IFN-ω belong to type I interferons (Liu et al., 2005). Type I interferons are typically produced by fibroblasts and monocytes in response to a viral infection. IFN-α has been shown to be beneficial in the treatment of hepatitis B and C infections, while IFN-β showed profound effects in the treatment of multiple sclerosis (Cohen, et al., 2001).

Type II interferons bind to IFNGR, which consists of IFNGR1 and IFNGR2 chains. The best known type II interferon in humans is IFN-γ (Cohen et al., 2001). IFNγ is predominantly produced by natural killer (NK) and natural killer T (NKT) cells as part of the innate immune response, and by CD4 Th1 and CD8 cytotoxic T lymphocyte (CTL) effector T cells once antigen-specific immunity has developed (Schoenborn et al., 2007). The importance of IFNγ in the immune system comes from its ability to inhibit viral replication directly, and most importantly from its immunostimulatory and immunomodulatory effects.

Type III interferons signal through a receptor complex consisting of IL10R2 and IFNLR1. Members of this family are known as interferon lamda (IFN-λ1, IFN-λ2, IFN-λ3). Although Type III interferons signal through distinct receptors, they elicit similar, but not fully redundant responses as type I interferons. In particular, IFN-λ has been shown to be very effective in controlling rotavirus infection, while the clearance of other viruses, such as influenza virus, is mostly dependent on the type I interferons, IFN-α and IFN-β. (Hermant et al., 2014).

IFN beta and especially the variant IFN-beta-1a is currently the most important interferon in the treatment of autoimmune diseases such as multiple sclerosis. Approved pharmaceutical compositions comprising IFN-β-1a include AvoneX® (Biogen Inc.) and Rebif® (EMD Serono Inc.). AvoneX® (Biogen Inc.). For the treatment of relapsing multiple sclerosis, AvoneX® is preferably injected intramuscularly and requires a dose of 30 µg once per week for adults (EMA, 2011). Rebif® also contains IFN-β-1a, but for this product the suggested dosing regimen is 44 µg three times a week administered by s.c. injection (EMA, 2014).

Preferably, the nanocarrier increases the stability of the drug. More preferably, the nanocarrier increases the stability of a peptide-or protein based drug and most preferably, the nanocarrier increases the stability of interferon beta. Determination of protein stability may be determined by methods known in the art, for example by sodium dodecyl sulfate polyacrylamide gel electrophoresis (SDS page).

Preferably, the drug is encapsulated within the nanocarrier as described elsewhere herein.

The encapsulation of a drug into a nanocarrier can occur by covalent or non-covalent binding. Furthermore, the nanocarrier and the drug can be reversible or non-reversible linked. Preferably, the linkage is a non-covalent, reversible linkage. Such non-covalent, reversible bonds are known in the art and include exemplary electrostatic interaction, van der Waals forces, hydrophobic effects, nanocarrierstreptavidin-biotin interaction and antibody-antigen interaction.

Preferably, a drug is encapsulated by mixing of a protein-based drug with a suitable nanocarrier, preferably heparin.

Moreover, the nanocarrier according to the present invention allows for slow release of the drug into the blood. "Slow release" of the drug, as meant herein, refers to the release or dosage form in which the active agent is released according to a desired profile over an extended period of time. Slow release profiles include, for example, sustained release, prolonged release, pulsatile release, and delayed release profiles. In contrast to immediate release compositions, slow release compositions allow delivery of an agent to a subject over an extended period of time according to a predetermined profile. Such release rates can provide therapeutically effective levels of agent for an extended period of time and thereby provide a longer period of pharmacologic or diagnostic response as compared to conventional rapid release dosage forms. Slow release compositions can further minimize side effects associated with inappropriate immediate release rates and optimize precise dosing. In the treatment of a variety of diseases, particularly for the treatment of autoimmune diseases such as multiple sclerosis, slow release formulations are often highly preferred over conventional short-acting formulations. In particular, slow release may indicate that after 24 hours less than 50% of drug has been released, preferably less than 40%, more preferably less than 30%. Alternatively, slow release may indicate that, after 48 hours, less than 50% of the active agent or active agent fraction has been released, preferably less than 40%, more preferably less than 30%, even more preferably less than 20%. Alternatively, slow release may indicate that, after 72 hours, less than 50% of the active agent or active agent fraction has been released, preferably less than 40%, more preferably less than 30%, even more preferably less than 20%.

It will be understood by those skilled in the art that the term "release of the drug into the blood" means that the drug shall be applied systemically, i.e. the composition comprising the drug is preferably intended for systemic application. In contrast to a local application, where drug shall exerts its effect directly at the at application site, in a systemic application, the drug shall enter the circulatory system so that the entire body is affected. Preferably, the composition intended for systemic application allows for dissociation into its individual components. More preferably, the nanocarrier and the drug are non-covalently linked and dissociate into individual components upon entering the blood stream. Most preferably, the composition intended for systemic application comprises heparin nanocomplexes.

Advantageously, it has been found in accordance with the studies underlying the present invention that a composition comprising two different matrices for drug delivery has improved release properties. In particular, the stability of the drug is safeguarded and the release can be prolonged and better controlled. The first matrix, i.e. the polymer, protects the nanocarriers upon injection or implantation into, e.g., a muscle, from immediate reactions in response to the injection/implantation. Moreover, the first matrix releases the drug which is still due to the nanocarriers in a protected and inactive state with an adjustable slow release kinetic. Upon release from the said polymer, the nanocarriers enter into the blood or other tissues where the drug is released again with an adjustable slow release kinetic from the nanocarrier. Thanks to the dual matrix system in the composition of the present invention, the release kinetic for the drug can be better adjusted since the final release kinetic for the drug depends on two individually adjustable kinetic parameters. Moreover, the drug and the nanocarrier are efficiently protected against immediate reactions upon injection or implantation by the polymer, i.e. a second protective layer.

The above explanations and definitions of the terms apply throughout the specification. Moreover, in the following, typical embodiments of the composition according to the present invention are listed.

In a preferred embodiment of the composition according to the present invention, said nanocarriers are covalently or non-covalently bound to the at least one biocompatible and biodegradable polymer.

In a further preferred embodiment of the composition according to the present invention, said biocompatible and biodegradable polymer is slowly swelling under physiological conditions.

In yet a preferred embodiment of the composition according to the present invention, said biocompatible and biodegradable polymer is selected from the group consisting of: polylactide (PLA), polyglycolide (PGA), polycaprolactone (PCL), polyhydroxyalkanoate (PHA), poly(ethylene-vinyl acetate) (PEVA), triglycerides, polysaccharides and proteins. More preferably, the biocompatible and biodegradable polymer comprises a polysaccharide.

Most preferably, the biocompatible and biodegradable polymer comprises methyl cellulose and/or hyaluronan.

In yet a preferred embodiment of the composition according to the present invention, said nanocarriers allow slow release of the drug into the blood.

In yet a preferred embodiment of the composition according to the present invention, said nanocarriers are polymer-based, protein-based or lipid-based nanocarriers.

In yet a preferred embodiment of the composition according to the present invention, said nanocarriers have an average size of less than 1000 nm, preferably, less than 500 nm, less than 300 nm, less than 200 nm, less than 100 nm or less than 50 nm.

In yet a preferred embodiment of the composition according to the present invention, said nanocarriers are heparin nanocomplexes.

In yet a preferred embodiment of the composition according to the present invention, said drug is a protein.

It will be understood that the present invention also provides the composition of the present invention for use in the treatment of a disease.

The term "treatment of a disease" as used herein refers to ameliorating or curing a disease or at least one symptom associated therewith. Thus, if there is amelioration or cure of the disease or at least a symptom associated therewith, the treatment shall be deemed to be effective. It will be understood that treating might not be effective in all subjects. However, according to the present invention it is envisaged that treatment will be effective in at least a statistically significant portion of subjects to be treated. It is well known to the skilled artisan how to determine a statistically significant portion of subjects that can be effectively treated. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the finding of effective treatment will be correct for at least 60%, at least 70%, at least 80%, or at least 90% of the subjects of a given cohort or population.

In a preferred embodiment of the present invention, said disease is an autoimmune disease.

The term "autoimmune disease" as used herein refers to a disease that arises from an abnormal immune response of the body against substances and tissues normally present in the body. Autoimmunity may affect the whole organism, may be restricted to certain organs, or may involve a particular tissue in different places. The diagnosis of an autoimmune disease is based on an individual's symptoms, findings from a physical examination, and results from laboratory tests. Typical tests for autoimmune diseases are known in the art and include blood tests, urine tests, swabs, diagnostic tests, lab tests, and pathology testing. However, some autoimmune diseases may be difficult to diagnose, especially in the early stages of the disease. Autoimmune diseases include systemic lupus erythematosus (SLE), sarcoidosis, scleroderma, rheumatoid arthritis, Diabetes mellitus type 1, Hashimoto's thyroiditis, Addison's disease, and multiple sclerosis.

In yet a preferred embodiment of the present invention, said autoimmune disease is multiple sclerosis (MS).

Multiple sclerosis (MS) is the most common autoimmune disease affecting the central nervous system. MS is a demyelinating disease in which the insulating covers of nerve cells in the brain and spinal cord are damaged. This damage disrupts the ability of parts of the nervous system to communicate, resulting in a wide range of signs and symptoms, including physical, mental, and sometimes psychiatric problems (Compston et al., 2008). MS takes several forms, with new symptoms either occurring in isolated attacks (relapsing MS forms) or build up over time (progressive MS forms). Between attacks, symptoms may disappear completely. However, as the disease advances, permanent neurological problems may appear (Reingold, 1996).

Relapsing-remitting multiple sclerosis (RRMS) is characterized by clearly defined attacks of worsening neurologic function. These attacks, the so-called relapses, appear over periods of at least 24 hours and are typically followed by partial or complete recovery periods (remissions), during which symptoms improve partially or completely, and there is no apparent progression of disease (Goldenberg, 2012). RRMS is the most common disease course at the time of diagnosis. Approximately 85 percent of people are initially diagnosed with RRMS, compared to 10-15 percent with progressive forms of the disease. SPMS (secondary-progressive multiple sclerosis) occurs in people who initially had a relapsing-remitting disease course (RRMS). In other words, SPMS occurs as a second phase of the disease for many individuals. Of the 85 percent of people who are initially diagnosed with RRMS, most will eventually transition to SPMS, which means that after a period of time in which they experience relapses and remissions, the disease will begin to progress more steadily, with or without any relapses.

It will be understood that the present invention also provides a method for manufacturing the said composition. In particular, provided is a method for manufacturing the said composition, said method comprising:

a) encapsulating a drug into nanocarriers;
b) generating a polymer matrix comprising at least one biocompatible and biodegradable polymer; and
c) incorporating the nanocarriers of step a) into the polymeric matrix of step b), whereby the composition is formed.

The term "encapsulating a drug" as used herein refers to any type of entrapment or incorporation of a drug within a polymer-, peptide- or lipid-based nanocarrier. Methods for encapsulating a drug are known in the art and include, but not limited to, precipitation, emulsion polymerization, interfacial condensation, freeze drying, supercritical fluid processing techniques, and co-acervation.

Preferably, a drug is encapsulated by mixing of a protein-based drug with a suitable nanocarrier, preferably heparin. Preferably, the mixture is incubated for at least one hour to induce complete precipitation. More preferably, the mixture is incubated for least one hour at a temperature around 20° C. and, optionally, a rotation of around 550 rpm. Further solidification of the nanocarriers encapsulating a drug is preferably done by freeze drying.

The encapsulation of a drug into a nanocarrier can occur by covalent or non-covalent binding. Furthermore, the nanocarrier and the drug can be reversible or non-reversible linked. Preferably, the linkage is a non-covalent, reversible linkage. Such non-covalent, reversible bonds are known in the art and include exemplary electrostatic interaction, van der Waals forces, hydrophobic effects, streptavidin-biotin interaction and antibody-antigen interaction.

Preferably, the encapsulation of a drug into a nanocarrier leads to a stabilization of the drug. Determination of the stability of a drug, especially a protein-based drug may be determined by methods known in the art, for example by sodium dodecyl sulfate polyacrylamide gel electrophoresis (SDS page).

In principle, nanocarriers can be manufactured as described elsewhere herein. More particular envisaged methods for the manufacture of nanocarriers are also described in US2003041602A, US2004197413A, U.S. Pat. Nos. 6,020,004A, 6,555,156B, WO9742940, Blume et al. 1990 and Wise, 1984. Particular preferred techniques in accordance with the present invention are disclosed in the accompanying Examples, below.

The term "generating a polymer matrix comprising at least one biocompatible and biodegradable polymer" refers to the establishment of biocompatible and biodegradable polymer polymer matrix. The polymer matrix comprising at least one biocompatible and biodegradable polymer is generated by methods known in the art, including, but not limited to, precipitation, emulsion polymerization, interfacial condensation, freeze drying, supercritical fluid processing techniques, and co-acervation.

Preferably the at least one biocompatible and biodegradable polymer is selected from the group consisting of: polylactide (PLA), polyglycolide (PGA), polycaprolactone (PCL), polyhydroxyalkanoate (PHA), poly(ethylene-vinyl acetate) (PEVA), triglycerides, polysaccharides and proteins. More preferably, the biocompatible and biodegradable polymer comprises a polysaccharide. Most preferably, the biocompatible and biodegradable polymer comprises methyl cellulose (MC) and/or hyaluronan (HA). Preferably, solutions of MC (1% [w/v]) and HA (1% [m/v]) are prepared in PBS pH 7.4, yielding a highly viscous polymeric matrix.

The term "incorporating" as used herein refers to a method of linking the nanocarriers to the polymeric matrix. Linkage of the nanocarrier and the polymeric matrix can occur by covalent or non-covalent binding. Furthermore, the nanocarrier and the polymeric matrix can be reversible or non-reversible linked. Preferably, the linkage is a non-covalent, reversible linkage. Such non-covalent, reversible bonds are known in the art and include exemplary electrostatic interaction, van der Waals forces, hydrophobic effects, streptavidin-biotin interaction and antibody-antigen interaction. Covalent bonds are characterized by the sharing of electron pairs between atoms. Covalent bond are known in the art and include σ-bonding, π-bonding, metal-to-metal bonding, agostic interactions, bent bonds, and three-center two-electron bonds.

All references cited in this specification are herewith incorporated by reference with respect to their entire disclosure content and the disclosure content specifically mentioned in this specification. Full citations of the references are to be found elsewhere herein.

FIGURES

FIG. 1: Freeze drying program used for the preparation of the precursor material for the implants. Running time was 89 h. Temperature (black line, ●) was decreased to −50° C. to enable primary drying and gradually elevated to +15° C. during secondary drying. Vacuum pressure (dotted line, ■) was to 0.006 mbar in order to assure sublimation during primary drying.

Figure 2:
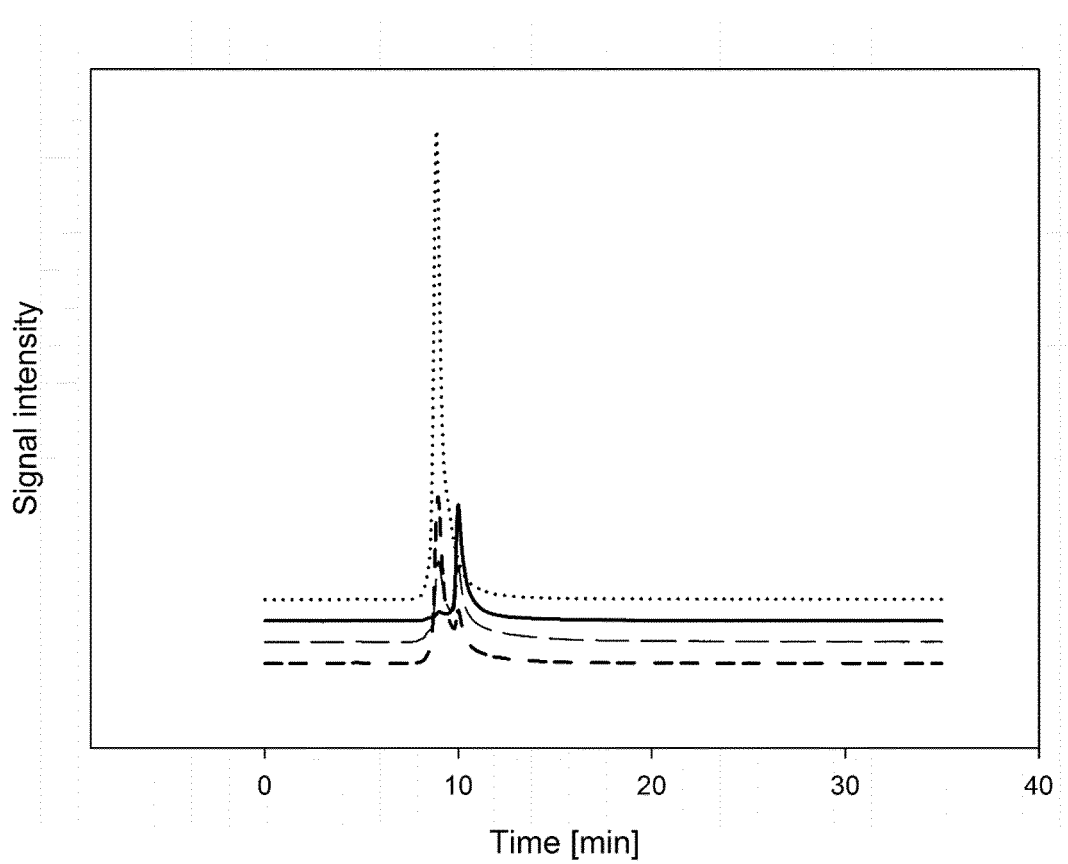

FIG. 2: SEC-diagram of trypsinogen [0.01 mg/mL, dotted line], trypsinogen-ATTO 647N-complex prepared at various DOL [0.5, short dash; 1, long dash; 3 black line]. Analysis was performed after removing the unbound dye by centrifugation through Micro Bio-Spin™ 6 chromatography columns. Retention time of the labeled complexes was increased compared to the native protein. Application of a DOL of 3 was sufficient for labeling more than 90% of the applied protein.

Figure 3:
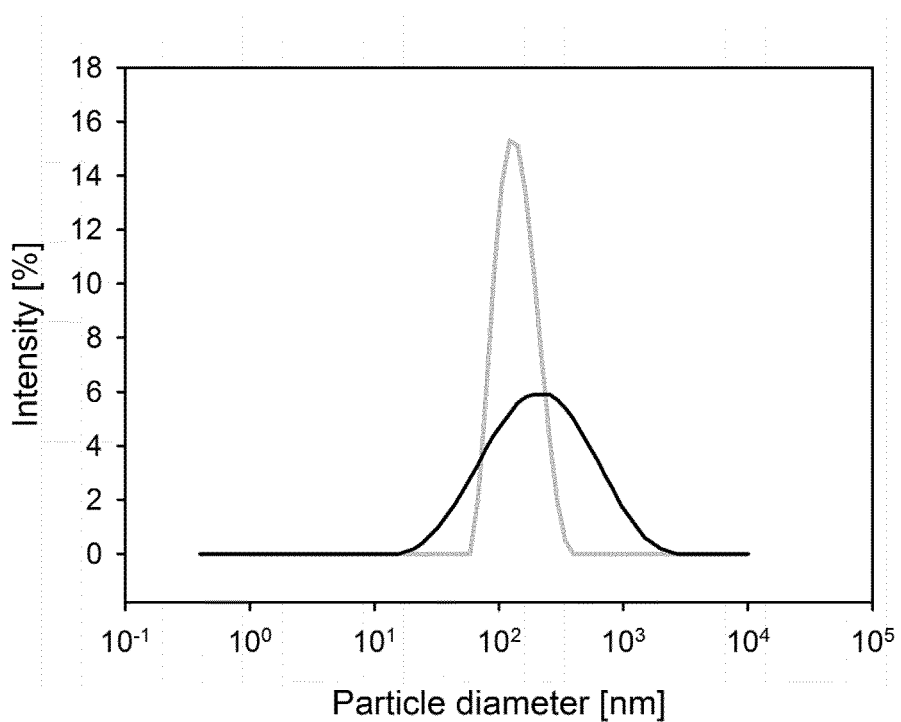

FIG. 3: Size distribution of trypsinogen-heparin-nanocomplexes (grey line) and IFN-β-heparin-nanocomplexes (black line) determined by DLS. The trypsinogen complex was diluted 50-fold before measurement. IFN-β-nanoparticles were measured undiluted in order to retrieve sufficient signal.

Figure 4:
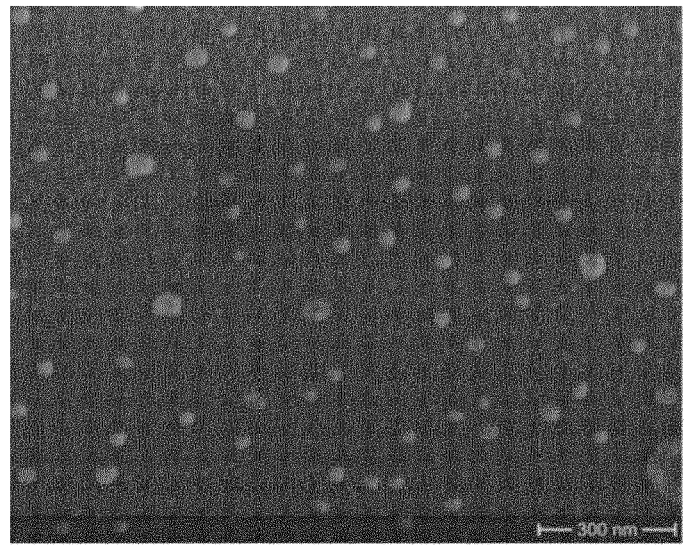
Figure 4:
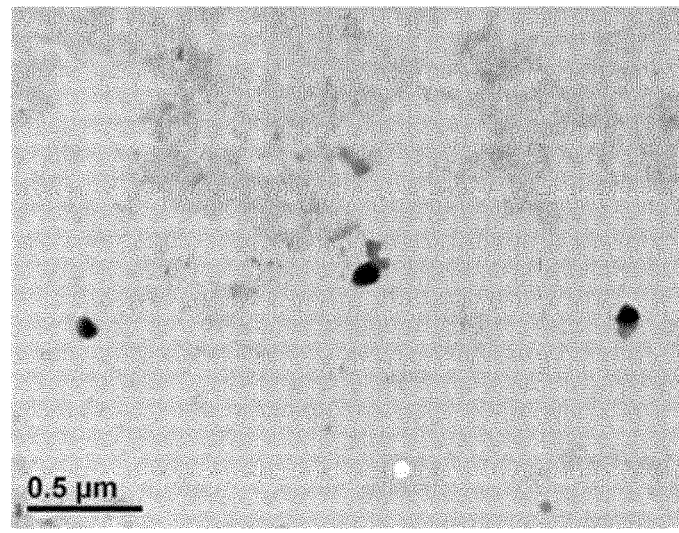
Figure 4:
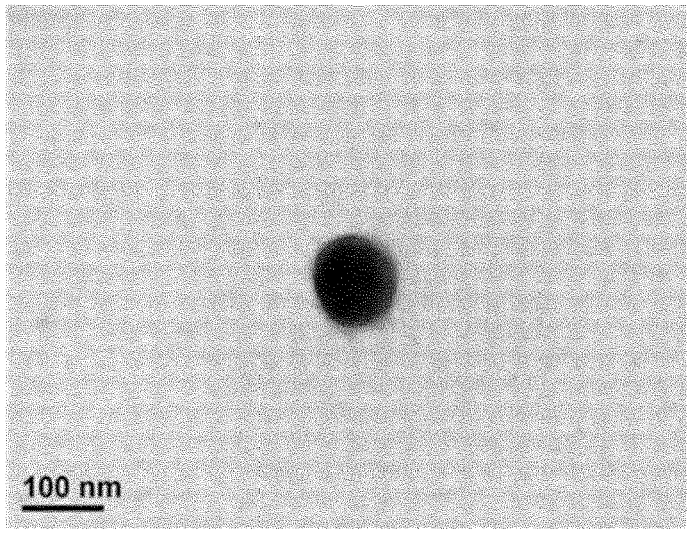

FIG. 4: Visualization of nanocomplexes by electron microscopy. The shape and size of the nanocomplexes were visualized with the help of scanning electron microscopy (SEM, A.) and transmission electron microscopy (TEM, B.,C.).

Figure 5:
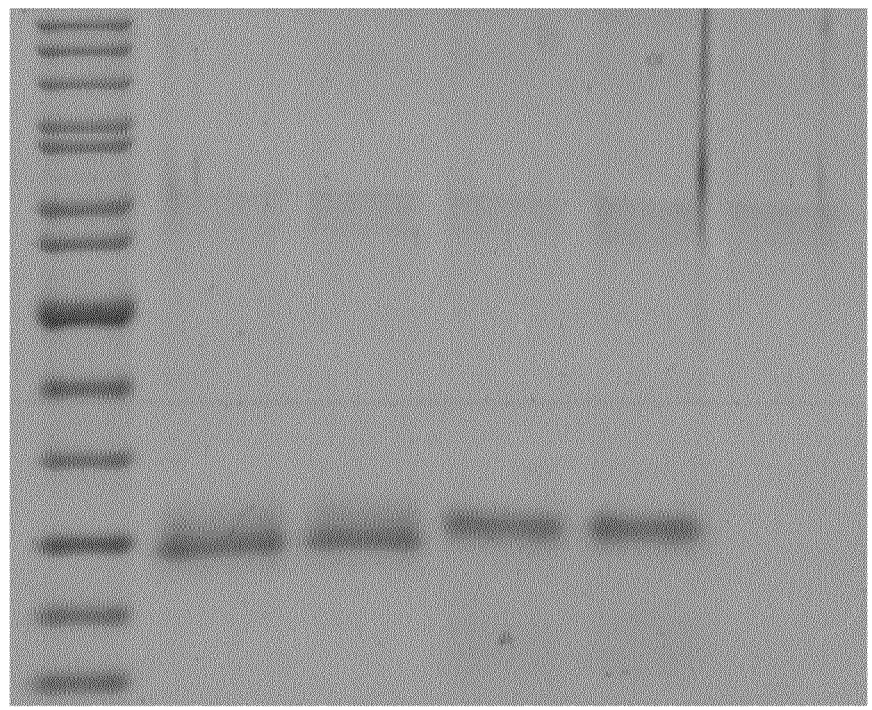

FIG. 5: SDS PAGE of PAGE ruler (lane 1) 1 μg IFN-β-1a (lane 2), re-hydrolyzed IFN-β-1a-heparin nanocomplex (lane 3), 1 μg trypsinogen (lane 4), re-hydrolyzed trypsinogen-heparin nanocomplexe (lane 5), and 1 μg heparin as control (lane 6, no band was observed). For the nanocomplexes amounts containing 1 μg of the protein (IFN-β or trypsinogen) were applied. No degradation or aggregation was observed for the processes proteins.

Figure 6:
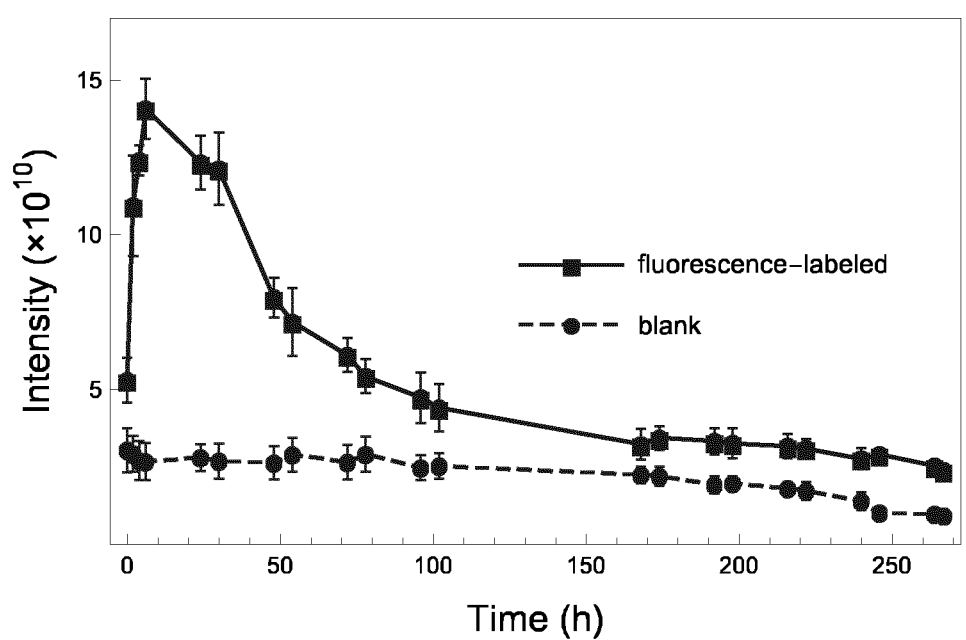

FIG. 6: Total radiance efficiency of the fluorescence signal observed in mice over a period of 12 days. The fluorescence-labeled implant (■) exhibited an elevated signal at all measured time point compared to the animals treated with a blank implant (●). The experiments were performed in triplicate. S.D. is used for descriptive error bars.

Figure 7:
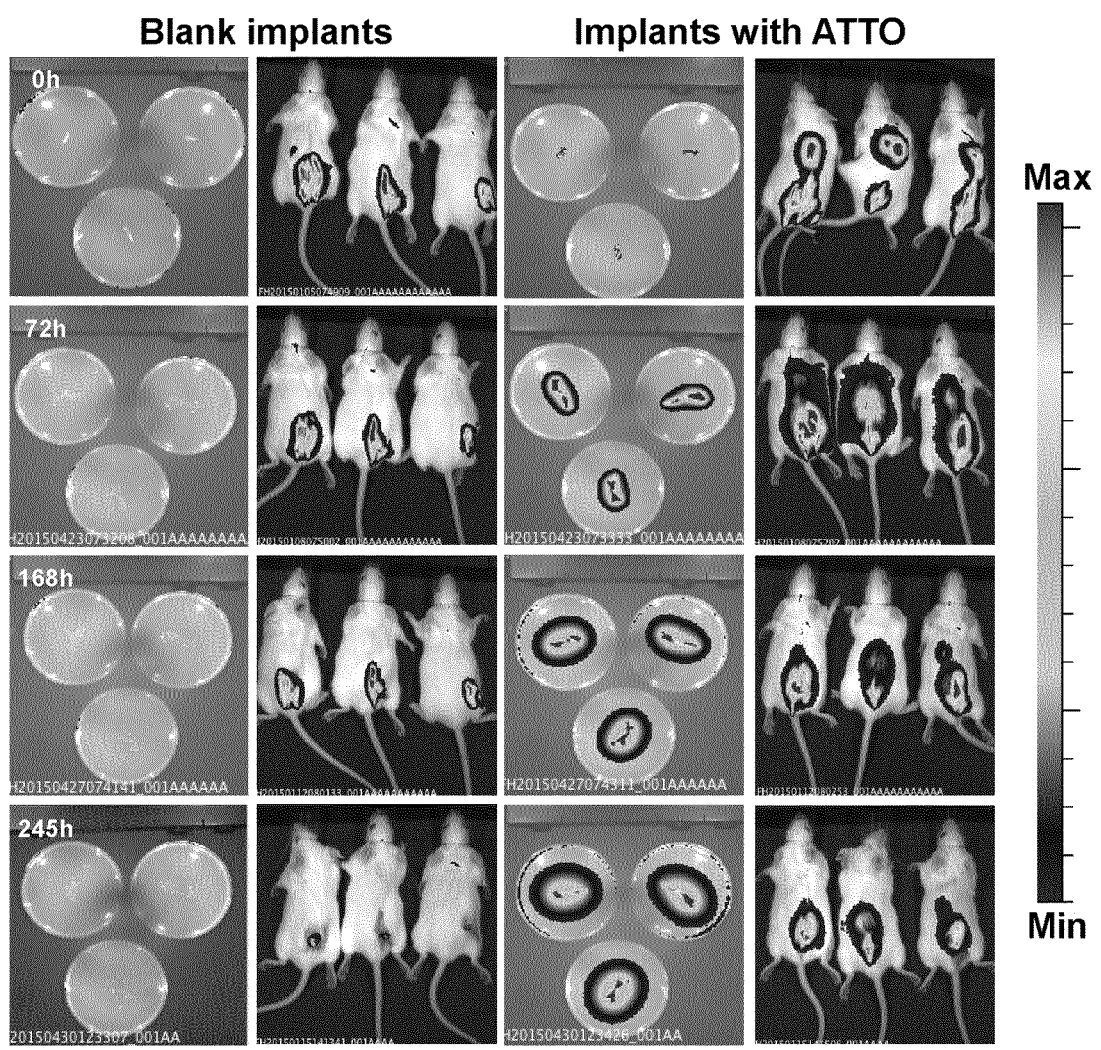

FIG. 7: Fluorescence imaging of in vitro and in vivo experiments on blank and fluorescence-labeled implants at 0 h, 72 h, 168 h and 245 h after experiments started. For in vitro experiments (columns 1&3), agarose gel with a concentration of 2% [w/v] was prepared in PBS pH 7.4 containing 10% [v/v] glycerol to mimic the subcutaneous fat tissue. For in vivo experiments (columns 2&4), implants with or without dye labeled were injected in the region of the neck.

Figure 8:
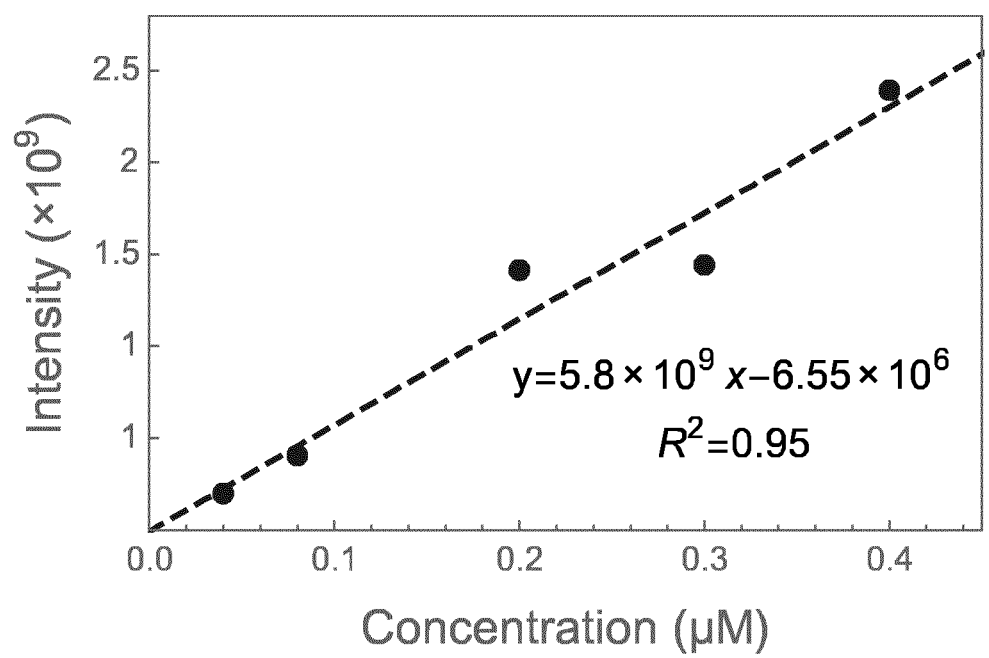

FIG. 8: Calibration for IVIS using agarose gel with different concentrations.

Figure 9:
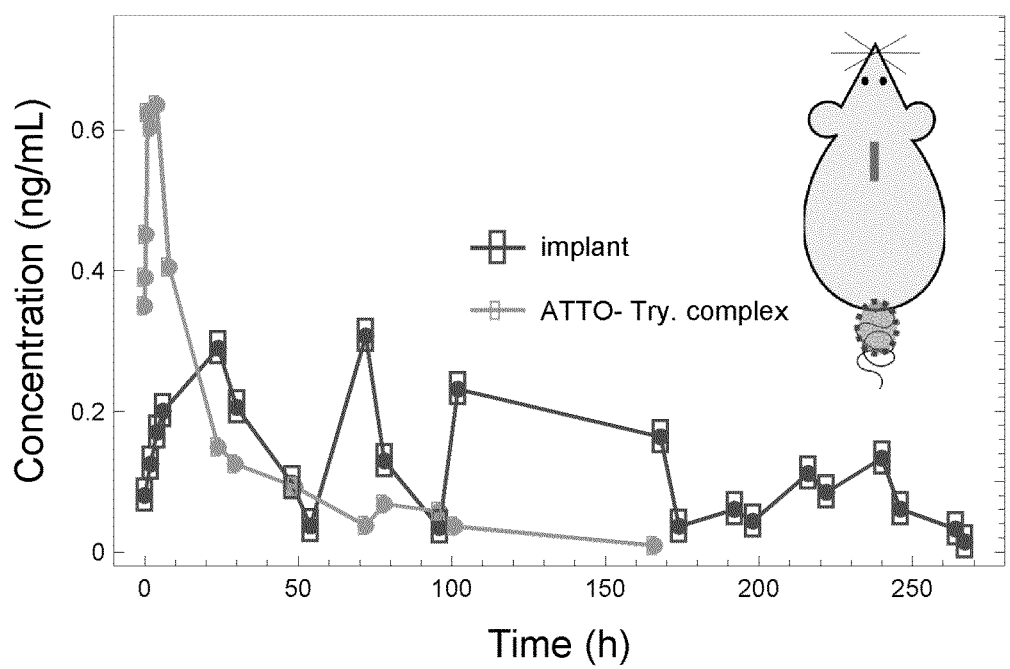

FIG. 9: Pharmacokinetic profiles for implants and ATTO-Trypsinogen suspension obtained in caudal region as ROI. Concentrations were calculated from the calibration.

Figure 10:
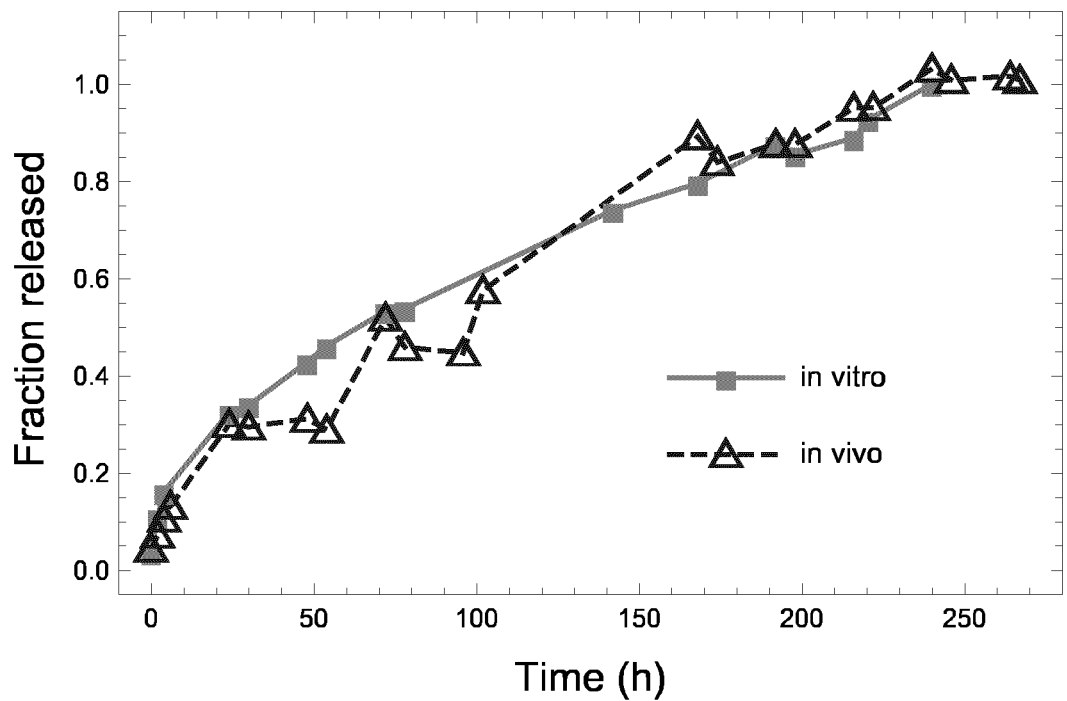

FIG. 10: Comparison of in vitro and in vivo release fractions for implants. In vitro release was performed using 2% agarose. Fraction released in vivo were calculated using Nelson-Wagner methods.

Figure 11:
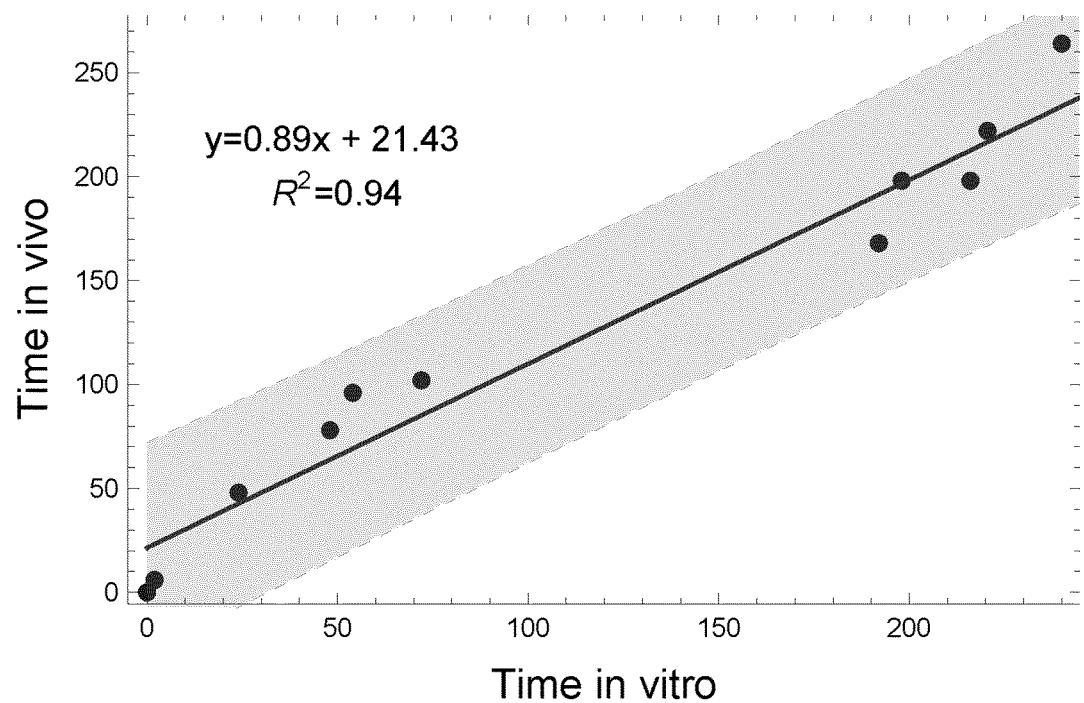

FIG. 11: IVIVC model linear regression plot of cumulative absorption and percent of dissolution. Grey area represents the confidence level of 95%.

EXAMPLES

The invention will be merely illustrated by the following Examples. The said Examples shall, whatsoever, not be construed in a manner limiting the scope of the invention.

Example 1: Preparation of Trypsinogen-Heparin Nanocomplexes

For the preparation of nanocomplexes, trypsinogen was dissolved in purified water to a concentration of 5 mg/mL. An aqueous heparin solution with a concentration of 50 mg/mL was added by one shot addition. The volume ratio was chosen as 1 part Heparin solution per 10 parts trypsinogen solution, consequently the weight ratio equaled 1:1. The mixture was incubated at 20° C. and 550 rpm for 1 h to induce complete precipitation.

Preparation of Interferon-β-1a-heparin Nanocomplexes:

The method described for the model compound trypsinogen was converted to the preparation of IFN-β particles. The concentration of the protein solution was modified, and selected to be 0.1 mg/mL due to the lower availability of IFN-β. Afterwards the heparin solution (50 mg/mL) was added. In this case the volume ratio was altered to 1 part heparin solution per 500 part IFN-β by preserving the weight ratio of both compounds. Incubation was performed as described for the trypsinogen-heparin-nanocomplexes.

Example 2: Determination of the Optimal Dye-to-Protein Ratio by Size Exclusion Chromatography and Quantification of the ATTO 647N-Protein Complex Concerning the SEC-analysis, a linear calibration was performed in the range of 0.025 to 0.6 mg/mL for trypsinogen. Retention time was found to be 9 minutes. Regarding the variation in DOL for the determination of optimal conditions concerning the binding reaction, FIG. 1 illustrates ascending ratios. The dye-protein complex can be determined by an increased retention time (10 minutes). The plot reveals that a DOL of 0.5 or 1 were not sufficient for binding trypsinogen quantitatively to the NHS-ester of ATTO 647N. At a DOL of 3, less than 1% of the applied trypsinogen remained unlabeled. Therefore for the preparation of fluorescence labeled IFN-β, a DOL of 3 was used. Previous studies have shown that an excess of unbound dye can be removed by centrifugation through Micro Bio-Spin™ 6 chromatography columns (Sax et al., 2012). Referring to the in vivo and in vitro-imaging experiments, a flux in the fluorescence signal can therefore be correlated to the diffusion of the labeled nanocomplexes out of the implant matrix that is attributed to their biodistribution.

Following the coupling reaction of protein and dye, the amount of the complex was determined spectrometrically at 647 nm which is the recommended wavelength for the analysis of the dye. The calibration was linear within the range of 4 to 70 μmol/L ATTO 647N-NHS-ester. Solutions obtained after the labeling procedure and filtration through the purification columns, were diluted by factor 100 and measured. At a DOL of 3; 78.37±4.87% of the applied dye was bound to the protein trypsinogen. Taking into account the results of the SEC-experiments, it appears than more than 90% of the applied protein was recovered in its labeled form.

Quantification of Trypsinogen by Size Exclusion Chromatography:

The HPLC-system for size exclusion chromatography (SEC) was composed of an LC-Organizer (Chromaster, VWR Hitachi, VWR International), a 5310 column oven, a 5450 refractive index detector, a 5260 auto sampler and an 5160 intelligent pump. As stationary phase a Biosep SEC-s3000 column (Phenomenex Inc., Aschaffenburg, Germany) was employed. The mobile phase was composed of phosphate buffered saline (PBS) at a pH-value of 6.8. Flow rate was set to 1 mL per minute; the observation wavelength was set to 280 nm. An injection volume of 30 μL was applied. Calibration was performed in the range of 0.025 to 0.6 mg/mL.

Coupling Reaction of Trypsinogen or Interferon-β to ATTO 647N NHS-Ester:

In order to label the protein with the photostable fluorescent dye ATTO 647N, a solution with a concentration of 5 mg/mL of the dyes NHS-ester in dimethyl sulfoxide was prepared. Solutions of the compounds IFN-β (0.1 mg/mL) or trypsinogen (5 mg/mL) were prepared in labeling buffer pH 8.3 containing PBS and sodium bicarbonate solution. Various dye-to-protein ratios (DOL) were tested with the model compound trypsinogen aiming to determine the optimal labeling procedure. Therefore, dye and protein solution were mixed and incubated in a reaction tube for 1 h at 20° C. and 550 rpm (Thermomixer Comfort, Eppendorf AG, Hamburg, Germany). Consequently the unbound dye was removed by filtration for 4 minutes at 1,000 rcf through Micro Bio-Spin™ 6 chromatography columns after buffer exchange. This method has been reported to be suitable for removing unbound dye (Sax et al., 2012).

Determination of the Optimal Dye-to-Protein Ratio:

For trypsinogen, the DOL was varied in order to transfer optimal conditions to the labeling reactions conducted with IFN-β. Therefore, molar ratios of 1:1; 1:2, and 1:3 (protein:dye) were analyzed. SEC analysis after filtration through Micro Bio-Spin™ 6 chromatography columns was performed in order to determine potential unlabeled protein.

Quantification of the ATTO 647N-Protein Complex:

A spectrometric method was applied to the quantification of the dye-protein complex after purification by filtration. Therefore, 100 µL of the samples or standard solution (native ATTO 647N-NHS ester in PBS pH 8.3) were pipetted into 96-well plates and measurement was performed with the microplate reader Infinite M200 (Tecan Group Ltdl, Crailsheim, Germany) at 647 nm. Calibration was performed in the range of 5.4×10-9 to 7×10-8 mol/mL.

Example 3: Characterization of Nanocomplexes by Dynamic Light Scattering

The particle size of the trypsinogen-heparin-nanocomplex was 152.6±4.8 nm. Size distribution as indicated by PDI was narrow (0.228±0.079) indicating the suitability of the obtained nanocomplexes for the parenteral application. Moreover, the stability in aqueous solutions was assured by a zeta potential of −53.2±2.3 mV.

Characteristics of the IFN-β-heparin nanocomplexes were determined to be 137.5±3.7 nm referring to the particle diameter (see FIG. 3). Size distribution was broader with a PDI of 0.470±0.024. Zeta potential was measured to be −27.4±4.1 mV. Experiments performed ahead of the establishment of the precipitation method revealed a strong influence of excipients and ions added during the preparation process due to an impact of osmolality and pH conditions on the precipitation process. Complexation and precipitation of two oppositely charged polyelectrolytes appears due to their coulombic forces. The hydrophilic parts of the molecules are neutralized during the complexation reaction. Therefore, hydrophobic properties increase which reduces their solubility in water (Boddohi et al., 2009; Tsuchida et al., 1972). Hence, any alteration in the composition of the aqueous medium emerges in altered intermolecular forces, such as hydrophobic bonding, hydrogen bonding, and electrostatic forces. The employed IFN-β-1a was lyophilized from a solution containing sodium chlorid (100 mN), sodium citrate (10 mM), and sucrose (10 mM) according to the supplier. Consequently, due to the changes in medium composition the mode of precipitation was altered, resulting in particles with a broader size distribution. However, the principles of the precipitation method could be applied to the generation of IFN-β-heparin nanocomplexes since the mean diameter was in a comparable range as seen for the trypsinogen-heparin complexes. A different processing of the IFN-β obtained from CHO-cells might help to overcome this problem. For example, the protein could be precipitated right after extraction or other stabilizers, influencing electrostatic forces less, could be used for lyophilisation.

In order to determine particle size, size distribution and net charge, a Zetasizer Nano ZS (Malvern Instruments GmbH, Malvern, UK) equipped with a backscatter detector at an angle of 173° was employed. Zeta potential as an indicator for net charge was analyzed by means of microelectrophoresis in a Malvern dip cell. The trypsinogen-based nanocomplexes were diluted by factor 10 before measurement, IFN-β-1a-based nanoparticles were measured undiluted.

Example 4: Determination of the Precipitation Yield

The yield of the established preparation method was determined for the trypsinogen-heparin-nanocomplexes due to their greater availability. After removing the unprecipitated heparin and trypsinogen by centrifugation and redispersion, the precipitation yield was determined gravimetrically and found to be 21±4.2%. This value might appear low at first sight, but it has to be taken into account that centrifugation at 20,800 rcf might still not be sufficient to separate particles smaller than 100 nm from the supernatant. A precipitation yield in the range of 10 to 25% was reported also for other heparin-based complexation processes (Boddohi et al., 2009). Moreover, purification by repetitive cycles of centrifugation and redispersion is not necessary for the prepared formulation due to the fact that no harmful additives or stabilizers were employed. Moreover, unprecipitated heparin could act as an anti-inflammatory and anti-fibrotic agent at the specific site of action. Therefore for the preparation of the implant no loss in the amount of applied API will appear in spite of the determined precipitation yield.

The amount of the precipitated trypsinogen-heparin nanocomplex was evaluated gravimetrically. Therefore, 1 mL of the nanoparticles suspension gained by precipitation was centrifuged at 20,800 rcf for 30 minutes at 4° C. The supernatant was removed with a pipette and the pellet was resuspended in 250 µL of purified water. After drying 50 µL of the particle suspensions for 2 hours at 80° C. on an aluminum dish, the amount was determined and expressed as percent of the originally applied compounds for precipitation.

Example 5: Visualization of Nanocomplexes by Electron Microscopy

SEM and TEM were used to determine the particle size and shape of the trypsinogen-heparin-nanocomplexes. Pictures taken by TEM assured the size measured by DLS. The shape appeared to be spherical for some of the particles, but also some with an irregular shape were detected. The observations by SEM revealed a significant amount of smaller particles which do not match the DLS-results completely. The irregular shape of some of the particles might disturb the evaluation of the algorithms based on the Raleigh Scattering that is used for the calculation of particle size (Tscharnuter et al., 2000). Nevertheless, nanocomplexes with a shape greater than 200 nm were not observed. Therefore, parenteral application of the established nanocarriers can be considered as uncritical.

The shape and size of the nanocomplexes were visualized with the help of transmission electron microscopy (TEM) and scanning electron microscopy (SEM). In case of TEM, 20 µL of the aqueous suspensions were transferred onto a coated copper grid. Staining was achieved by treatment with phosphotungstic acid solution (2% [w/v]). A transmission electron microscope model CM 12 (Philips, Amsterdam, The Netherlands) equipped with a Gatan module 782 (ES 500 W) was used.

For the SEM analysis, aliquotes of 20 µL were pipetted onto an SEM-sample holder and allowed to dry for 24 h. Afterwards, sputtering with gold was performed by means of an Agar Sputter Coater (Agar Scientific, Essex, UK). The device used was a Hitachi S4500 microscopy system (Hitachi, Tokyo, Japan).

Example 6: Generation of Implants Containing the Nanocomplexes

By freeze drying and pressing, preformed implant were prepared with a diameter of 2 mm, a length of 8 mm, and a weight of approximately 20 mg. The composition of the matrix containing MC and HA assures a good safety profile combined with a prolonged release of the API due to the excellent swelling properties of the polymer. In situ-forming implant often exhibit a burst release of the API during formation of the depot system (Kempe et al., 2012). Moreover, often organic solvents such as N-methyl-2-pyrrolidone or ethanol cannot be neglected, but administration might be accompanied by toxic effects (Leira et al., 1992; Malek et al., 1997). The developed preformed implant was constituted of well-established and biocompatible excipients. The precise control of size also enables administration with an implant syringe. Although needles are quite large, this is regarded as beneficial in contrast to an application by incision. No further preparation before the administration is necessary which depicts another advantage compared to in situ-forming systems. Since the final product is a solid dosage form, the absence of water in the final formulation design is prone to prevent protein instability like aggregation or denaturation.

Solidification of the nanocomplexes was assured by freeze drying. Therefore a highly viscous gel matrix was used for developing an implant with a prolonged release in vivo. Hence solutions of MC (1% [w/v]) and HA (1% [m/v]) were prepared in PBS pH 7.4. 1 g of each component was applied per vial in order to achieve sufficient material for one implant. The amount of protein added was selected with regard to the administered dose of the commercially available products. Because the implant developed in the present study is intended for the s.c. administration, Rebif® was used as a reference. The administered dose comprises 44 µg three times per week. Preliminary in vivo-experiments of the implant formulation established in our study suggested that fluorescence signal could be determined for two week in mice. Hence, the calculated dose would be 44 µg×3 times per week×2 week of endurance. For human beings 264 µg per implant would therefore be considered appropriate. Due to the difference in weight (approximately 75 kg for humans and 20 g per mouse), the adjusted dose would be 70 ng per mouse. However, the number of dye molecules per protein was reported to be low (approximately 1 to 3) (Sax et al., 2012). Therefore, for the presented study 1×10-8 mol referred to ATTO 647N-NHS were added per vial. Assuming, that 3 molecules ATTO 647N-NHS-Ester bind per molecule protein, 80 ng trypsinogen were incorporated per implant. The solutions were freeze dried for 89 h with the device Christ Epsilon 2-4 LSC (Martin Christ Gefriertocknungsanlagen GmbH, Osterode, Germany). The program used is visualized in FIG. 1. Afterwards, the implants were obtained by pressing the lyophilisates into cylindrical shape. Therefore, a manual implant press specially designed and constructed for this purpose was used.

Example 7: Determination of Protein Stability by Sodium Dodecyl Sulfate Polyacrylamide Gel Electrophoresis Processing of the protein by precipitation with heparin and the step of incubation in an aqueous medium might induce degradation of the protein structure. Therefore, an SDS PAGE was run in order to compare the unprocessed compounds IFN-β and trypsinogen with their corresponding nanocomplex containing heparin. FIG. 5 visualizes that IFN-β and trypsinogen are characterized by a comparable molecular weight (see lanes 2 and 4). Precipitation with heparin did not induce the formation of dimer fractions in neither of these formulations (see lane 3 and 5). Aggregation or degradation of the proteins would have been recognized by additional bands, but even hydrolysis in PBS pH 8.0 did not result in stability problems. Therefore, structure of the proteins was obtained throughout the preparation process promoting the suitability of the preparation process. The formation of aggregates is often described as an obstacle in the generation of sustained release formulation of proteins which was overcome with the prepared formulation (Morlock et al., 1997; Sinha et al., 2003). Heparin as a polysaccharide was not visualized after coomasie blue staining.

The process of precipitation represents stressful conditions for the protein. Shaking in an aqueous medium and the interaction with the polysaccharide heparin might induce aggregation. To exclude this effect, sodium dodecyl sulfate polyacrylamide gel electrophoresis (SDS page) was performed. Therefore, 100 µL, of the heparin nanocomplexes of IFN-β and trypsinogen were centrifuged at 20,800 for 15 min at 4° C. The pellet was hydrolyzed in 50 µL, PBS pH 8.0. Solutions containing 2 µg IFN-β or trypsinogen in 10 µL aqueous solutions were diluted with 10 µl Schaegger buffer and cooked for 5 min. As controls unprocessed IFN-β, trypsinogen, and heparin (final concentrations: 2 µg in 20 µL, including Schaegger buffer) were applied. PAGE ruler was applied to the first lane to detect protein size. Electrophoresis was performed under standard conditions.

Example 8: Pharmacokinetic in SJL-Mice

Tracking the fluorescence intensity with the IVIS assured a prolonged release over twelve days. Even after this period the fluorescence was still elevated compared to the implant not containing the dye (see FIG. 6). Therefore, the selection of matrix material showed great potential towards the development of a novel innovative drug delivery system. Moreover, the fluorescence signal observed in animals that carried a blank implant (containing the trypsinogen-heparin nanocomplex in the described matrix, but not containing any dye) excluded an inflammatory response to the formulation. Mice did show not any sign of infection or stress during the period of observation. Therefore, the formulation can be considered as uncritical. However, a period of two weeks might still not be sufficient to promote the implants for an administration to patients. Nevertheless, the formulation process is adjustable by a multitude of parameter. Hence, by an enlargement of the implants dimensions by increasing diameter or length the matrix and diffusion pathways could be increased which can prolong the residence time. The specially designed implant press also allows the adjustment of hardness. Consequently, the weight of the preformed implants can easily be increased without a need for altering dimensions. This might enhance the release time as a result of decreased pore size in the matrix material.

The in vivo-imaging analysis was performed by IVIS® technology. The device IVIS® Lumina Spectrum (Perkin Elmer, Waltham, Mass., USA), enabled observation of bioluminescence and fluorescence signals, which were evaluated with the Living Image software (Perkin Elmer, Waltham, Mass., USA). Therefore, the implants were administered to female SJL-mice subcutaneously by a minimal invasive incision in the region of the neck. Implants containing the trypsinogen-ATTO 647N-heparin nanocomplex were contrasted to a corresponding formulation containing trypsinogen-heparin nanocomplexes in the MC/HA-matrix without any dye. This control allows for the evaluation of fluorescence that is caused by irritations due to the process of implantation and helps to evaluate a possible inflammatory response to the formulation. For each experiment three mice were tested. Over a time period of eleven days the mice were anesthetized at selected time points and the flux in the fluorescence signal was determined. Therefore, an emission wavelength of 700 nm and an excitation wavelength of 640 nm were used.

Example 9: In Vivo-In Vitro Correlation

The release properties of subcutaneous tissue were simulated by conducting in vitro experiments from a 2% [w/v] agarose gel. The gel was prepared with PBS pH 7.4 containing 10% [v/v] glycerol. A volume of 50 mL of the mixture was poured into a petri-dish. All implants were manufactured as described above and placed in the center of this release compartment. The drug release was monitored by using IVIS® technology.

Implants were prepared in absence of ATTO 647N to serve as a reference. Fluorescence intensity was measured at predetermined time points. FIG. 7 shows the imaging results of the in vivo and the in vitro experiments after 0 h, 72 h, 168 h and 245 h. To quantify the fluorescence intensity of these images, total radiance efficiency was measured for fluorescence intensity applying IVIS software.

Because s.c. injection was performed in the neck region on the mouse back, the signal detected in the dorsal area can include fluorescence in subcutaneous tissue and in blood circulation. Therefore, fluorescence intensity of the caudal region was set as region of interest (ROI) for correlating with plasma concentration. Plasma concentrations were calculated from fluorescence intensity by using the calibration curve plotted in FIG. 9. The $c_{max}$ values (peak plasma concentration) determined for the implants and the ATTO-trypsinogen suspension were 0.306 ng/mL and 0.656 ng/mL, respectively.

There was a $t_{max}$ value (time to reach $c_{max}$) of 9 h observed for the implants and of 6 h for the suspension. It should be noticed that the fluctuations in the plasma concentration of implant experiments can be explained by the slow release of the implant at the injection site.

To establish the relationship between drug released in vitro and in vivo, the fraction absorbed was determined from the plasma concentration profile by deconvolution using the Nelson-Wagner (J. G. Wagner et al., 1963) method and linear trapezoidal rule. The elimination rate ($k_{el}$=0.068 h$^{-1}$) was obtained from the slope of the linear portion of the curve by least square regression analysis (G. Schliecker et al., 2003). Thus, FIG. 10 presents the percentage of drug absorbed in vivo and the drug amount released in vitro against time. The sampling time in vitro was plotted against the corresponding time points in vivo (FIG. 11) in a levy plot. FIG. 11 suggests a good correlation ($R^2$=0.94) of the release profiles in vitro and in vivo.

REFERENCES

Abe et al. (2007), Low molecular weight heparin prevents hepatic fibrogenesis caused by carbon tetrachloride in the rat. J Hepatol 46(2), 286-294.

Alam et al. (2015), Functionalized heparin-protamine based self-assembled nanocomplex for efficient anti-angiogenic therapy. J Control Release 197, 180-189.

Balazs et al. (1989), Clinical uses of hyaluronan. The biology of hyaluronan 265, 285.

Blume et al. (1990), Liposomes for the sustained drug release in vivo, Biochimica et Biophysica Acta 1029 (1): 92-97.

Boddohi S et al. (2009), Polysaccharide-based polyelectrolyte complex nanoparticles from chitosan, heparin, and hyaluronan. Biomacromolecules 10(6), 1402-1409.

Brownsey et al. /2003), The glass transition behavior of the globular protein bovine serum albumin. Biophysical journal 85.6, 3943-3950.

Cohen et al. (2001). An overview of the immune system. Lancet 357 (9270): 1777-89.

Compston A et al. (2008). "Multiple sclerosis". Lancet 372 (9648): 1502-17.

De Weerd et al. (2007). Type I interferon receptors: biochemistry and biological functions. J Biol Chem 282 (28): 20053-20057.

Dowdy and Wearden (1983), Statistics for Research, John Wiley & Sons, New York.

EMA (2011), European Public Assessment Report on Avonex (Interferon-beta-1a), EMA/354496/2011.

EMA (2014), European Public Assessment Report on Rebif (Interferon-beta-1a), EMA/14511/2014.

Funk et al. (2005), Safety and efficacy of Implanon™, a single-rod implantable contraceptive containing etonogestrel. I.U.S. Group. Contraception 71(5), 319-326.

Goldenberg (2012), Multiple sclerosis review. Pharmacy and Therapeutics 37(3), 175.

Gupta et al. (2006), Fast-gelling injectable blend of hyaluronan and methylcellulose for intrathecal, localized delivery to the injured spinal cord. Biomaterials 27(11), 2370-2379.

Hermant et al. (2014), Interferon-λ in the Context of Viral Infections: Production, Response and Therapeutic Implications. J Innate Immun, April 17.

Hohlfeld (1997), Biotechnological agents for the immunotherapy of multiple sclerosis. Principles, problems and perspectives. Brain 120(Pt 5), 865-916.

I.M.S.S. Group (1993), Interferon beta-1b is effective in relapsing-remitting multiple sclerosis I. Clinical results of a multicenter, randomized, double-blind, placebo-controlled trial. Neurology 43(4), 655-655.

Kempe et al. (2012), In situ forming implants—an attractive formulation principle for parenteral depot formulations. J Control Release 161(2), 668-679.

Langer-Gould et al. (2004), Strategies for managing the side effects of treatments for multiple sclerosis. Neurology 63(11 Suppl 5), S35-41.

Leira et al. (1992), Irritant cutaneous reactions to N-methyl-2-pyrrolidone (NMP). Contact Dermatitis 27(3), 148-150.

Li et al. (2001a), Gel network structure of methylcellulose in water. Langmuir 17(26), 8062-8068.

Li et al. (2001b), Randomized controlled trial of interferon-beta-1a in secondary progressive MS MRI results. Neurology 56(11), 1505-1513.

Li et al. (2015), Low molecular weight heparin (LMWH) improves peritoneal function and inhibits peritoneal fibrosis possibly through suppression of HIF-1alpha, VEGF and TGF-beta1. PLoS One 10(2).

Liang et al. (2000), A novel heparin/protamine-based pro-drug type delivery system for protease drugs. J Pharm Sci 89(5), 664-673.

Liu et al. (2005). IPC: professional type 1 interferon-producing cells and plasmacytoid dendritic cell precursors. Annu Rev Immunol 23: 275

Liu et al. (2007), Heparin/chitosan nanoparticle carriers prepared by polyelectrolyte complexation. J Biomed Mater Res A 83(3), 806-812.

Malek, et al. (1997), Repeated dose toxicity study (28 days) in rats and mice with N-methylpyrrolidone (NMP). Drug and chemical toxicology 20(1-2), 63-77.

Mank et al. (1991), Parenteral depot drug forms with a base of biodegradable polymers. Pharmazie 46(1), 9-18.

Morlock et al. (1997), Microencapsulation of rh-erythropoietin, using biodegradable poly (D, L-lactide-co-glycolide): protein stability and the effects of stabilizing excipients. European Journal of Pharmaceutics and Biopharmaceutics 43(1), 29-36.

Pecly et al. (2006), Effects of low molecular weight heparin in obstructed kidneys: decrease of collagen, fibronectin and TGF-beta, and increase of chondroitin/dermatan sulfate proteoglycans and macrophage infiltration. Nephrol Dial Transplant 21(5), 1212-1222.

Portaccio et al. (2009), Improving compliance with interferon-β therapy in patients with multiple sclerosis. CNS drugs 23(6), 453-462.

Reder et al. (2014), How type I interferons work in multiple sclerosis and other diseases: some unexpected mechanisms. J Interferon Cytokine Res 34(8) 589-599.

Reingold (1996). "Defining the clinical course of multiple sclerosis: results of an international survey". Neurology 46 (4): 907-11).

Sadzak et al. (2008), Recruitment of Stat1 to chromatin is required for interferon-induced serine phosphorylation of Stat1 transactivation domain. Proc Natl Acad Sci USA 105(26), 8944-8949.

Sarkar (1979), Thermal gelation properties of methyl and hydroxypropyl methylcellulose. Journal of Applied Polymer Science 24(4), 1073-1087.

Sax et al. (2012), Release pathways of interferon alpha2a molecules from lipid twin screw extrudates revealed by single molecule fluorescence microscopy. J Control Release 162(2), 295-302.

Schliecker et al. (2003), In vitro and in vivo correlation of buserelin release from biodegradable implants using statistical. doi: 10. 1016/j.jconrel.2003.09.003.

Schoenborn et al. (2007), Regulation of interferon-gamma during innate and adaptive immune responses. Adv. Immunol. 96: 41-101.

Sinha et al. (2003), Biodegradable microspheres for protein delivery. J Control Release 90(3), 261-280.

Spagnoli et al. (2005), Hyaluronan conformations on surfaces: effect of surface charge and hydrophobicity. Carbohydrate research 340(5), 929-941.

Sudha et al. (2014), Beneficial effects of hyaluronic acid. Adv Food Nutr Res 72, 137-176.

Tate et al. (2001), Biocompatibility of methylcellulose-based constructs designed for intracerebral gelation following experimental traumatic brain injury. Biomaterials 22(10), 1113-1123.

Tscharnuter (2000), R. A. Meyers (Ed.), Encyclopedia of Analytical Chemistry, John Wiley & Sons Ltd, Chinchester, 2000, pp. 5469-5485.

Tsuchida et al. (1972), Interaction of poly (styrene sulfonate) with polycations carrying charges in the chain backbone. Journal of Polymer Science Part A-1: Polymer Chemistry 10(11), 3397-3404.

Wagner et al. (1963), Percent absorbed time plots derived from blood level and/or urinary excretion data, Journal of pharmaceutical sciences, vol. 52, pp. 610-611.

Wise (1984), Biopolymeric Controlled Release Systems, Vol. 1, Wise, ed., CRC Press Inc., Chapter 8.

Zhou et al. (1998), Development of a multiple-drug delivery implant for intraocular management of proliferative vitreoretinopathy. Journal of Controlled Release 55(2), 281-295.

The invention claimed is:

1. A composition comprising at least one biocompatible and biodegradable polymer, said at least one biocompatible and biodegradable polymer comprising nanocarriers comprising at least one of a polymer, protein, lipid or combination thereof and at least one immunomodulatory protein drug,
    wherein the nanocarriers are covalently or non-covalently bound to the at least one biocompatible and biodegradable polymer, and the at least one immunomodulatory protein drug is non-covalently linked to said nanocarriers,
    wherein said nanocarriers are protected by said at least one biocompatible and biodegradable polymer from immediate reaction upon in vivo administration of said composition,
    wherein the at least one immunomodulatory protein drug is trypsinogen or interferon (IFN) beta, and the at least one immunomodulatory protein drug is released from said composition with a controlled release kinetic after in vivo administration of said composition, and
    wherein the at least one biocompatible and biodegradable polymer has a half-life in the order of 1 to 8 weeks upon in vivo administration.

2. The composition of claim 1, wherein the at least one biocompatible and biodegradable polymer is selected from the group consisting of: polylactide (PLA), polyglycolide (PGA), polycaprolactone (PCL), polyhydroxyalkanoate (PHA), poly(ethylene-vinyl acetate) (PEVA), triglycerides, polysaccharides, and proteins.

3. The composition of claim 1, wherein said nanocarriers allow controlled release of the immunomodulatory protein drug into the blood.

4. The composition of claim 1, wherein the nanocarriers have an average size of less than 1000 nm, less than 500 nm, less than 300 nm, less than 200 nm, less than 100 nm or less than 50 nm.

5. The composition of claim 1, wherein said nanocarriers are heparin nanocomplexes.

6. The composition of claim 1, wherein the at least one immunomodulatory protein drug is IFN beta.

7. The composition of claim 1, wherein the at least one immunomodulatory protein drug is trypsinogen.

8. The composition of claim 6, wherein said IFN beta is IFN beta 1a.

9. A method for treatment of a disease comprising administering to a subject suffering from the disease a therapeutically effective amount of the composition according to claim 1 wherein the disease is multiple sclerosis.

10. A method for manufacturing the composition of claim 1 said method comprising:
    a) Encapsulating the at least one immunomodulatory protein drug into nanocarriers;
    b) generating a polymer matrix comprising the at least one biocompatible and biodegradable polymer; and
    c) incorporating the nanocarriers of step a) into the polymeric matrix of step b), whereby the composition is formed.

11. The composition of claim 3, wherein said controlled release of the the immunomodulatory protein drug into the blood is sustained release, prolonged release, pulsatile release, or delayed release.

* * * * *